United States Patent [19]

Campopiano

[11] Patent Number: 5,397,322
[45] Date of Patent: Mar. 14, 1995

[54] MANIPULATOR FOR EXTERNAL BONE FIXATION DEVICES

[75] Inventor: Ascanio Campopiano, Torre del Greco, Italy

[73] Assignee: Jaquet Orthopedie S.A., Geneva, Switzerland

[21] Appl. No.: 965,269
[22] PCT Filed: Aug. 1, 1991
[86] PCT No.: PCT/IT91/00071
§ 371 Date: May 25, 1993
§ 102(e) Date: May 25, 1993
[87] PCT Pub. No.: WO92/02184
PCT Pub. Date: Feb. 20, 1992

[30] Foreign Application Priority Data

Aug. 3, 1990 [IT] Italy ............................ 40434/90

[51] Int. Cl.⁶ ............................................. A61B 17/60
[52] U.S. Cl. ......................................... 606/57; 606/54
[58] Field of Search ..................... 606/54, 55, 56, 57, 606/58, 59, 53, 72, 73

[56] References Cited

U.S. PATENT DOCUMENTS

| | | | |
|---|---|---|---|
| 4,604,997 | 8/1986 | DeBastiani et al. | 606/55 |
| 4,607,625 | 8/1986 | Schenck | 606/55 |
| 4,628,919 | 12/1986 | Clyburn | 606/55 |
| 4,922,896 | 5/1990 | Agee et al. | 606/55 |
| 4,988,349 | 1/1991 | Pennig | 606/58 |
| 5,100,403 | 3/1992 | Hotchkiss et al. | 606/56 |
| 5,122,140 | 6/1992 | Asche et al. | 606/55 |
| 5,160,335 | 11/1992 | Wagenknecht | 606/59 |

FOREIGN PATENT DOCUMENTS

| | | |
|---|---|---|
| 177270 | 4/1986 | European Pat. Off. . |
| 248138 | 12/1987 | European Pat. Off. . |
| 414633 | 2/1991 | European Pat. Off. . |
| 512792 | 11/1992 | European Pat. Off. . |
| 3305597 | 8/1984 | Germany . |

Primary Examiner—Stephen C. Pellegrino
Assistant Examiner—Guy V. Tucker
Attorney, Agent, or Firm—Peter C. Richardson; Lawrence C. Akers; Raymond W. Augustin

[57] ABSTRACT

A manipulator for reducing a bone fracture has adjustable elements for manipulating external fixation devices which are connected to the bone segments on either side of the fracture. The manipulator includes a circular sector having a first half sector portion and a second half sector portion. The sector portions are coupled for relative sliding movement therebetween for extending and retracting the arc of said circular sector. The manipulator includes a locking element for locking the first and second half sector portion at selected relative positions. Each of said first and second half sector portions has a generally cylindrical recess formed at the outer end thereof.

A pair of cylindrical bushings having an outer cylindrical surface with teeth extending parallel to a longitudinal axis of the bushings are provided. One of the cylindrical bushings are rotatably mounted in each of the generally cylindrical recesses in the first and second half sector portions. Each of the cylindrical bushings are coupled to the respective external fixation device via a shaft extending from the bushing in a direction perpendicular to the longitudinal axis thereof.

A drive element engages the longitudinally extending teeth on each of the bushings for rotating the bushing so that the angle of the shaft with respect to the half sector portions can be varied.

7 Claims, 5 Drawing Sheets

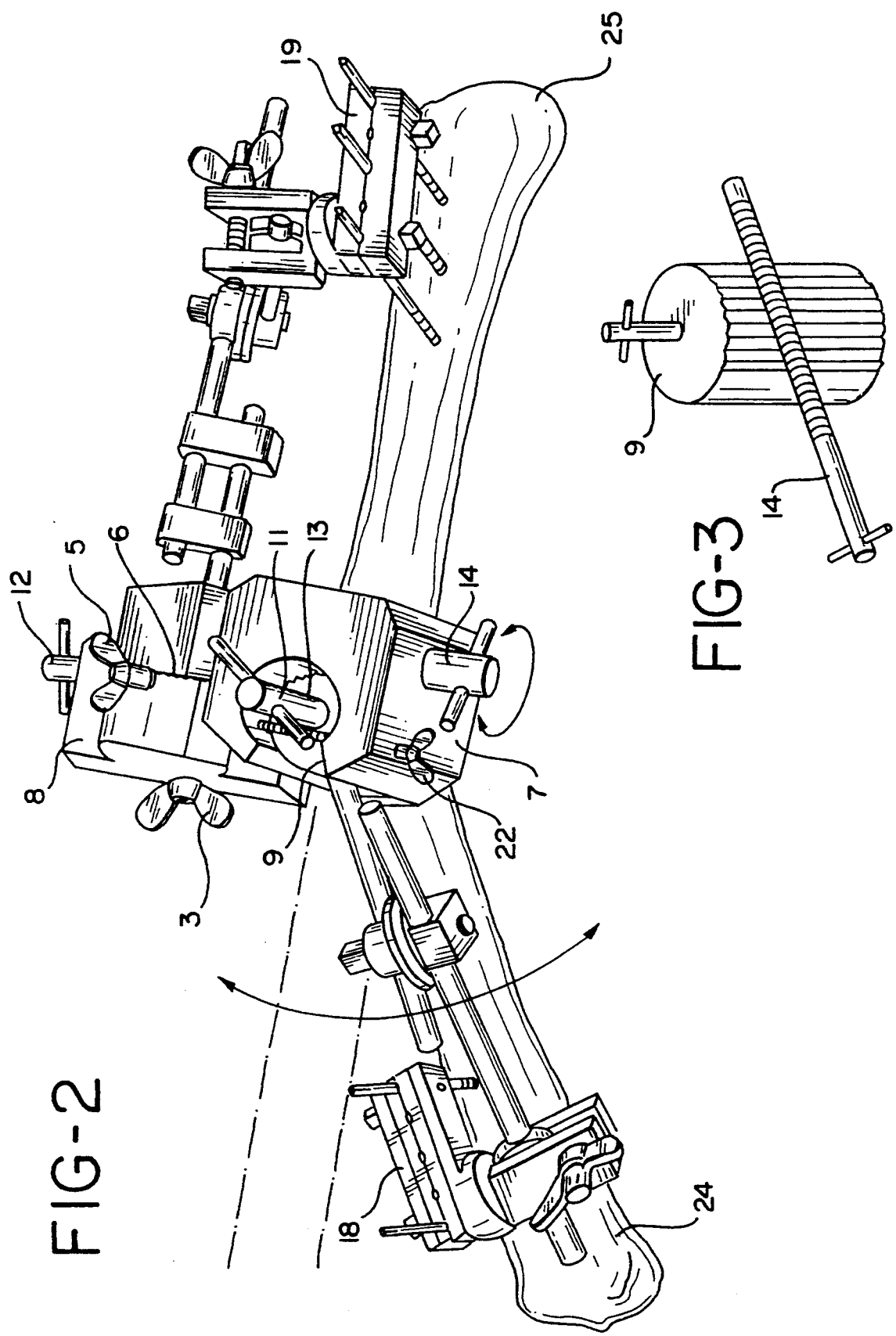

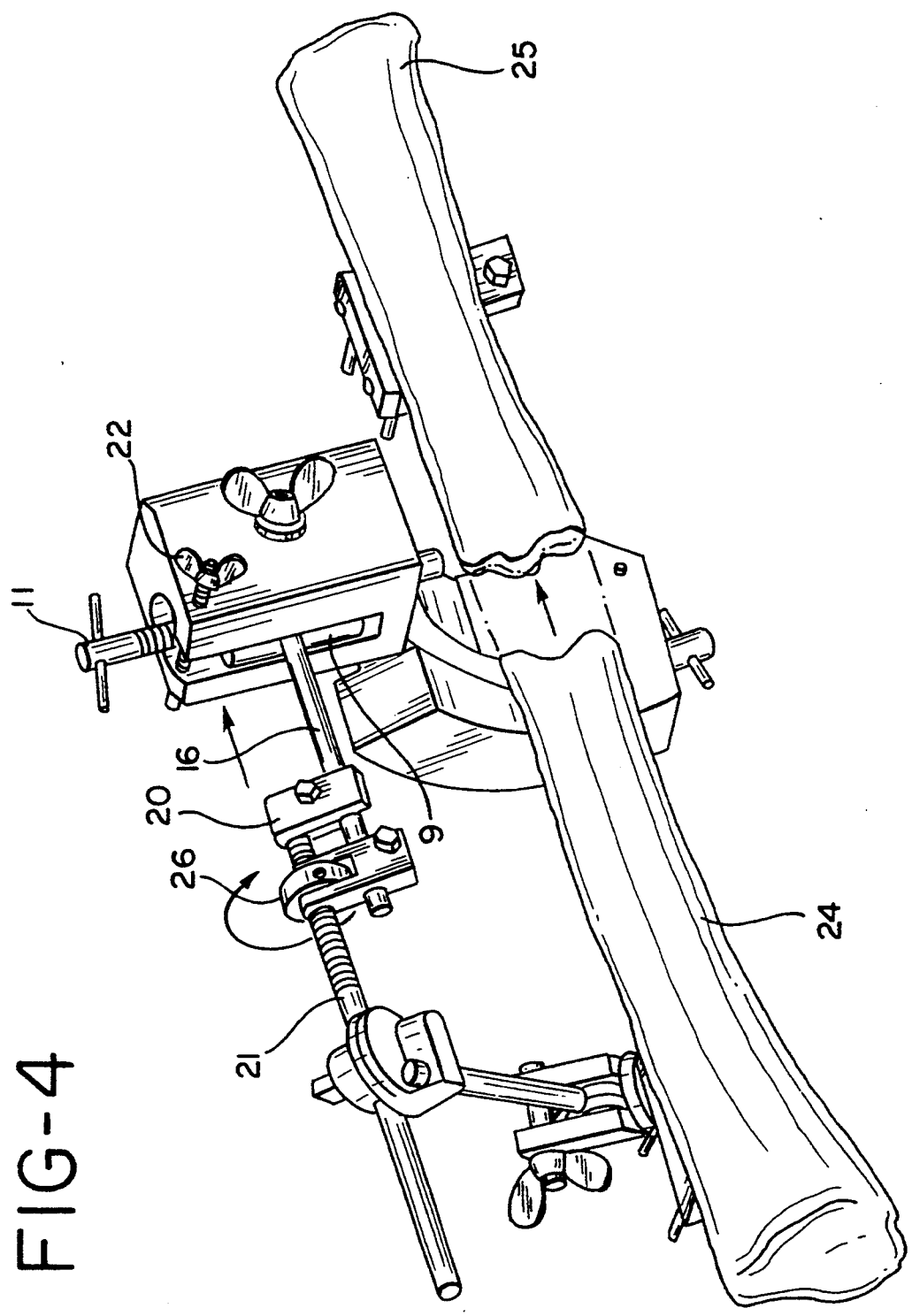

1 …

MANIPULATOR FOR EXTERNAL BONE FIXATION DEVICES

Field of the Invention

Description of the Prior Art

External bone fixation for the therapy of skeletal fractures of limbs has been in use for many years in traumatologic medicine.

External fixation substitutes the use of immobilizing plastering apparatuses which always involve a long rehabilitation, and, at the same time, often avoids an operation in open air.

However, it is often a difficulty using a manipulator for performing reduction to obtain an optimum anatomic reconstruction of the fractured skeletal segment.

The various commercially available external fixator systems do not allow such fracture manipulation, or they allow them only partially. Their placement therefor risks often making the already obtained reduction result worse, and often with a complicated and approximative mechanical structure. Manipulators available are not suitable to be applied to any external fixing system and can not be removed from the system, after having performed the necessary fracture reduction manoeuvers.

Movements allowed with currently used manipulators do not necessarily concern the fracture section and require action on more than one key.

SUMMARY OF THE INVENTION

It is an object of the present structure industrial invention to suggest a means that makes the reduction manoeuvers easier by allowing micrometric (small) displacements of the bone fragments to be reduced.

It is an additional object of the invention to allow the reduction manoeuvers to be practised independently of each other, so as not to compromise the already obtained fracture reduction result.

The manipulator of the present invention is intended to be removed or to remain applied to a limb through the proper fixation elements, and to this end it is provided with clamping members that ensure a stable maintenance of the position reached during reduction. Furthermore, its geometrical construction allows all monuvements to take place in the fracture section.

The present invention is realized by a manipulator which allows, by acting upon proper screw handlebar grips, a micrometric displacement of the fractured bone fragments in all the possible directions realizing all the degrees of freedom and all the required relative axial and angular rotations.

BRIEF DESCRIPTION OF THE DRAWINGS

The manipulator shown in a preferred embodiment thereof is given as a matter of example and not of limitation in the annexed drawings.

FIG. 2 is a top isometric view the manipulation of angular rotation in the horizontal plane made possible by the manipulator of the present invention;

FIG. 3 illustrates the particular mating between the toothed sector and the endless screw that allows some rotation manoeuvers;

FIG. 4 shows in a rear isometric view the possible maneuver for the axial slide of the fragments;

DESCRIPTION OF THE PREFERRED EMBODIMENT

Figure 1:
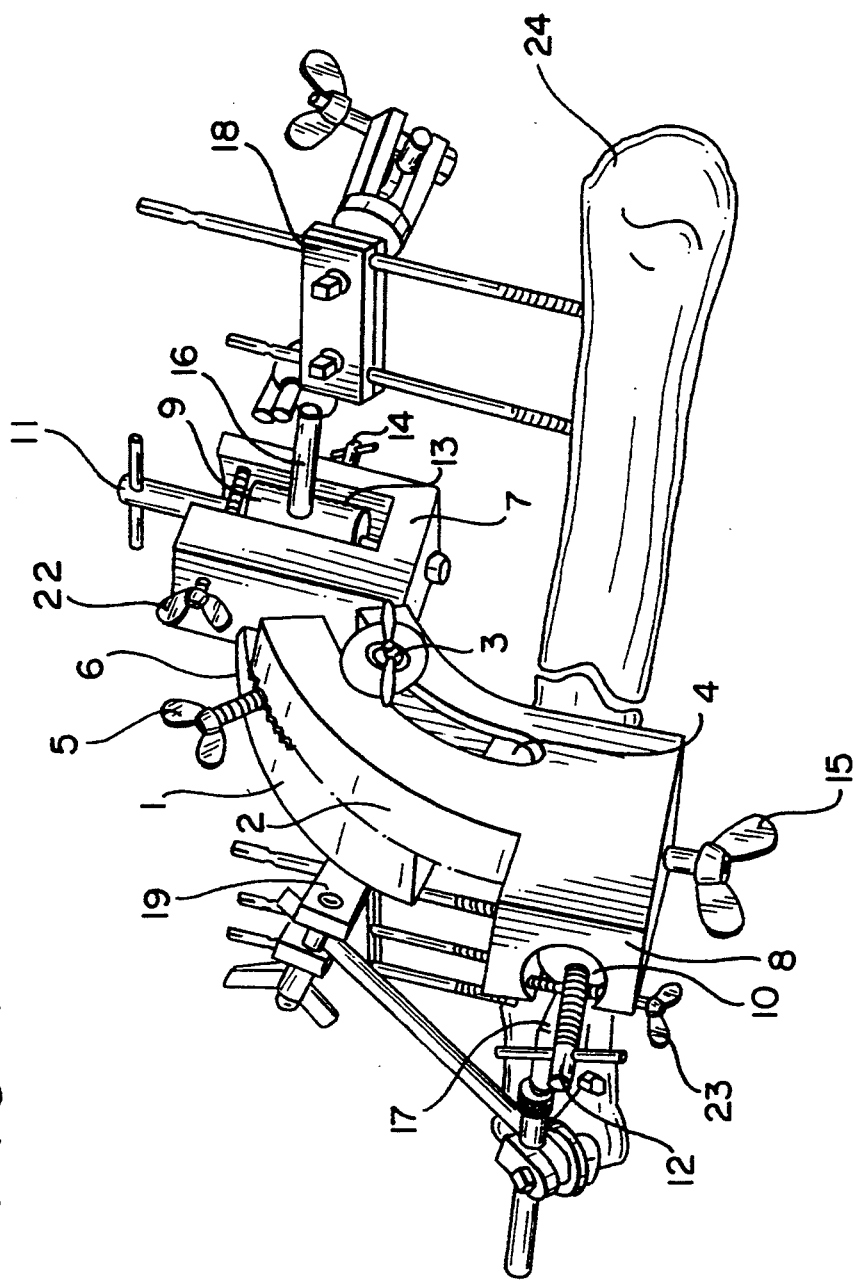
FIG. 1 is an axonometric front side view that shows it in the stage of its utilization applied to a fixer of a known type.
Figure 5:
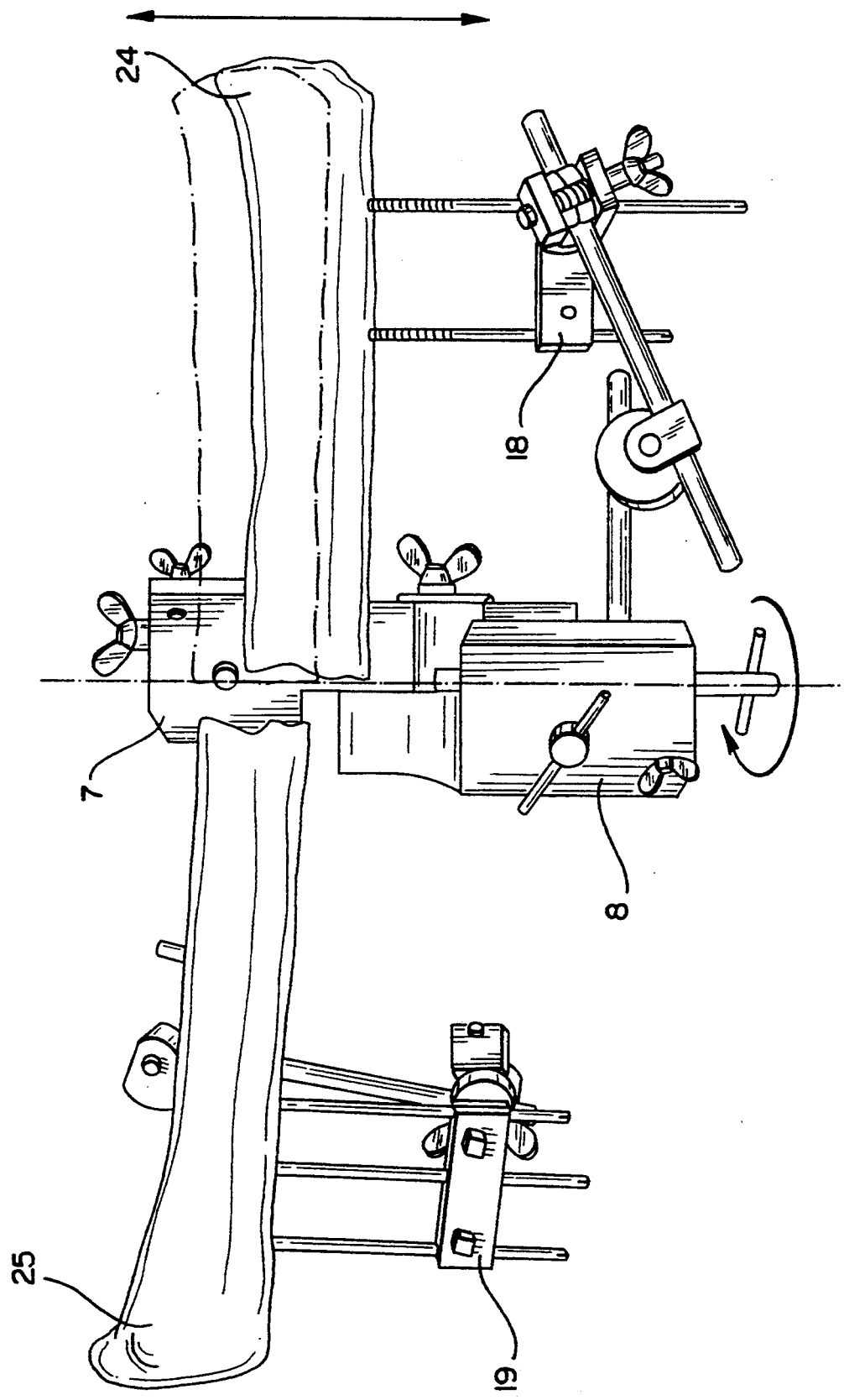
FIG. 5 represents the manipulator in a rear isometric view that shows the manoeuver for the transverse slide in the horizontal plane.
Figure 6:
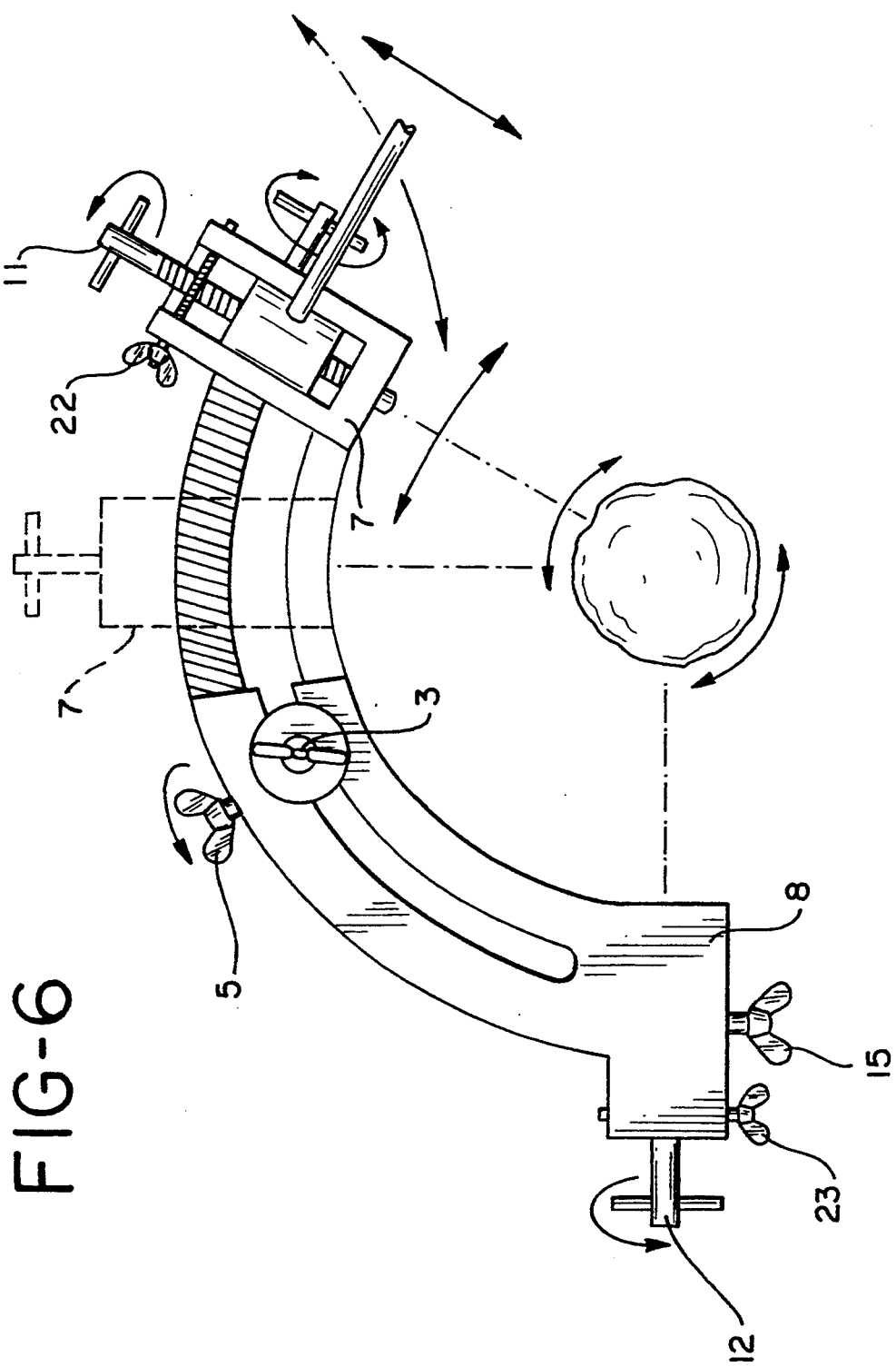
FIG. 6 is a front view of the detail of the sector that allows the axial rotation of the fragments.

With reference to the figures, the manipulator is made up of a sector that extends a quarter of a circle and is comprised of two half sector portions 1 and 2 having guides fit for sliding angularly on each other. A screw 3 that is located in a slit 4 which goes through a large part of sector 2 is loosened to allow the relative sliding movement of portions 1 and 2.

In this way the sector arc can be varied from about 60° to about 120°.

A screw 5 engages with teeth 6 which are provided on a portion of the contact faces of the two sectors 1 and 2 and allows a micrometric displacement of one sector portion with respect to the other.

Each sector portion at the end which is not slidably engaged projects respectively into or is formed integral with blocks 7 and 8. Blocks 7 and 8 are shaped having a recess to receive bushings 9 and 10. Bushing 9 and 10 are displaced by the screws 11 and 12 and have along a portion of their cylindrical surface teeth 13 that respectively engage the teeth of screws 14 and 15. The teeth of screws 14 and 15 are slightly angled with respect to the orthogonal axis of the screw itself, as shown in FIG. 3.

From bushings 9 and 10 stems 16 and 17 project, which by means of a suitable coupling system end at and are connected to, the clamps of the fixators 18 and 19. On the stem 16 a slid coupling, 20 is provided which connects it to the slide bar 21 or some other axial slide system.

Such a structure may be realized through a slide bar a known external fixation device or, will be able to be realized with any other slide system that acts along the longitudinal axis of the bar of the bar of the manipulator.

The recesses in blocks 7 and 8 include moderately elastic and transverse screws 22 and 23 fit to tighten them in order to clamp the motion of the internal bushings 9 and 10;

From what has been illustrated it is apparent that by acting upon the described screws the following displacements of the bony fragments 24 and 25 connected to the relevant clamps of the external fixation device can be performed:

a) by acting upon the screw 26 of the device or other known axial slide system one determines the approaching or the removal of the fragments along the longitudinal axis;

b) by acting upon the screw 12 one determines the transverse translation in the vertical plane of the fragment 24 with respect to the fragment 25:

c) by acting upon the screw 11 one determines the transverse translation in the horizontal plane of the fragment 25 with respect to the fragment 24;

d) by acting upon the screws 14 and 15 one adjusts the relative angle of the fragments in the vertical and horizontal plane;

e) Finally by acting upon the screw 5, one determines the angular displacement of the two half-sectors 1 and 2 and thus the rotation of the fragments about their own axis.

The geometric characteristics that are required in the design of the fixator are: the coplanarity of the longitudinal axes of 11 and 12 and the convergence of these axes into the fracture focus.

When the fracture has been reduced, the screws 3 and the screws 22 and 23 are tightened, so as to clamp the manipulator in its final position. In this position it can remain applied to the limb for possible subsequent adjusting manoeuvers. This is made possible by its reduced size and by its extremely restricted weight.

It is however also possible to remove it by clamping the fixator elements 18 and 19 with a simple connector of a known type.

The light weight and smallest encumbrance characteristics are a consequence of the solutions adopted for the realization of all the movements that occur according to the suggested invention with an extremely compact instrument.

Formal and structural variations can be made to the invention without departing from the scope of the invention, which is defined by the following claims.

I claim:

1. A manipulator for reducing a bone fracture by manipulating external fixation devices connected to the bone segments on either side of the fracture, the manipulator comprising:

a circular sector defining an arc having a first half sector portion and a second half sector portion, said portions coupled for relative sliding movement therebetween for extending and retracting the arc of said circular sector and including a locking element for locking the first and second half sector portion at selected relative positions, each of said first and second half sector portions having a generally cylindrical recess formed at an outer end thereof;

a pair of cylindrical bushings having an outer cylindrical surface with teeth extending parallel to a longitudinal axis of said bushings, one of said cylindrical bushings rotatably mounted in each of said generally cylindrical recesses in said first and second half sector portions, each of said cylindrical bushings having a shaft extending from said bushing in a direction perpendicular to said longitudinal axis of said bushings for coupling to the respective external fixation device; and a drive element for engaging said longitudinally extending teeth on each of said bushings for rotating said bushing so that the angle of said shaft with respect to said half sector portions can be varied.

2. The manipulator of claim 1 wherein said drive element is a screw extending in a direction perpendicular to said longitudinal axis of said bushings and having teeth thereon for engaging said longitudinal teeth on said bushings.

3. The manipulator of claim 1 wherein said arc of said circular sector may be extended or retracted to form an arc of between 60° and 120°.

4. The manipulator as set forth in claim 1 wherein said longitudinal axis of said bushing is coaxial with a longitudinal axis of said recess and said axes of the recess in said first and second half sector portions lie in the same plane and converge on the fracture site.

5. The manipulator of claim 4 wherein an adjustment element acts between said cylindrical bushings and said recesses to provide movement therebetween along said longitudinal axes.

6. The manipulator of claim 5 wherein said adjustment element is a screw captured by each half sector portion and operatively engaging each bushing.

7. The manipulator of claim 6 wherein said first and second half sector portions are coupled for sliding engagement along contact faces which may be displaced from one another by a screw extending perpendicular to said arc of said circular sector.

* * * * *